United States Patent [19]
Day et al.

[11] Patent Number: 5,448,070
[45] Date of Patent: Sep. 5, 1995

[54] IDENTIFICATION OF UNKNOWN GASES USING INFRARED ABSORPTION SPECTROSCOPY

[75] Inventors: Stephen Day, Duxbury; Kailash Swarna, Bridgewater, both of Mass.

[73] Assignee: The Foxboro Company, Foxboro, Mass.

[21] Appl. No.: 65,997

[22] Filed: May 21, 1993

Related U.S. Application Data

[63] Continuation-in-part of Ser. No. 62,593, May 17, 1993, abandoned.

[51] Int. Cl.$^6$ .................................................. G01J 3/02
[52] U.S. Cl. ........................... 250/339.13; 250/339.07; 364/498
[58] Field of Search ............ 250/338.5, 339.01, 339.07, 250/339.13, 347; 364/498

[56] References Cited

U.S. PATENT DOCUMENTS

| | | | |
|---|---|---|---|
| 2,775,160 | 12/1956 | Foskett et al. | 356/418 |
| 3,428,401 | 2/1969 | Buzza | 356/417 |
| 4,527,062 | 7/1985 | Novinson | 250/351 |
| 4,818,875 | 4/1989 | Weiner | 250/343 |
| 5,023,804 | 6/1991 | Hoult | 364/498 |
| 5,311,445 | 5/1994 | White | 364/498 |

FOREIGN PATENT DOCUMENTS

| | | |
|---|---|---|
| 0307082 | 3/1989 | European Pat. Off. . |
| 1505913 | 4/1978 | United Kingdom . |
| 1560943 | 2/1980 | United Kingdom . |

OTHER PUBLICATIONS

G. Hangac et al., "Compression of an Infrared Spectral Library by Karhunen–Loeve Transformation", Applied Spectroscopy, vol. 26, No. 1, 1982.

*Primary Examiner*—Paul M. Dzierzynski
*Assistant Examiner*—David Vernon Bruce
*Attorney, Agent, or Firm*—Fish & Richardson

[57] ABSTRACT

A method and apparatus for identifying an unknown gas by generating an infrared spectrum of the unknown gas using an infrared spectrophotometer that includes a circular variable interference filter, compressing the infrared spectrum of the unknown gas, and comparing the compressed infrared spectrum of the unknown gas to a library of compressed infrared spectra of reference compounds. After comparison, the compressed spectra that most closely match the unknown gas are decompressed and displayed. Because frequency characteristics of circular variable interference filters vary from filter to filter, information designating these frequency characteristics for the particular filter employed are used in generating the infrared spectrum of the unknown gas.

15 Claims, 4 Drawing Sheets

Microfiche Appendix Included
(1 Microfiche, 49 Pages)

| | 1 | 2 | 3 | 4 | 5 | 6 | 7 | 8 | 9 | 10 |
|---|---|---|---|---|---|---|---|---|---|---|
| 52: | 1 | 1 | 3 | 1 | 1 | 2 | 4 | 6 | 4 | 1 |
| 54: | 2 | 3 | 3 | 3 | 3 | 4 | 3 | 2 | 2 | 2 |
| 56: | 1 | 1 | 4 | 2 | 2 | 2 | 3 | 7 | 5 | 2 |

D54: $(1)^2 + (2)^2 + (0)^2 + (2)^2 + (2)^2 + (2)^2 + (1)^2 + (4)^2 + (2)^2 + (1)^2 = 39$

D56: $(0)^2 + (0)^2 + (1)^2 + (1)^2 + (1)^2 + (0)^2 + (1)^2 + (1)^2 + (1)^2 + (1)^2 = 7$

IDENTIFICATION OF UNKNOWN GASES USING INFRARED ABSORPTION SPECTROSCOPY

CROSS REFERENCE TO RELATED APPLICATIONS

This application is a continuation-in-part of 08/062,593 an application by Stephen Day and Kailash Swarna entitled "IDENTIFICATION OF UNKNOWN GASES USING INFRARED ABSORPTION SPECTROSCOPY" and filed on May 17, 1993 abandoned.

REFERENCE TO MICROFICHE APPENDIX

A microfiche appendix is attached to this application. The appendix, which includes software for implementing portions of an unknown gas identification system according to the invention, includes 49 frames on 1 microfiche.

BACKGROUND OF THE INVENTION

The present invention relates to spectroscopy, and more particularly to the use of infrared absorption spectroscopy in identification of an unknown gas.

Infrared absorption spectroscopy involves generating an infrared spectrum for a material such as a gas or vapor. A material's infrared spectrum is a measure of the tendency of the material to absorb infrared energy having wavelengths that vary across a predetermined band of infrared wavelengths. For example, many applications use the mid-infrared spectral band, which includes wavelengths from 2.5 micrometers to approximately 14 micrometers. The material's infrared spectrum is generated by measuring the degree of absorption for each wavelength in the spectrum, and plotting absorption versus wavelength.

Different chemical compounds produce vastly differing characteristic spectral profiles or "signatures" over the mid-infrared spectral band, by which they can be readily recognized. Thus, to identify an unknown gas, the infrared spectrum of the unknown gas is visually or mathematically compared with the infrared spectra of a number of reference gases. By comparing the unknown spectrum with a library of reference compounds, the most likely match to the unknown gas can be determined. If the shape of the infrared spectrum of the unknown gas matches that of the infrared spectrum of a reference gas within a defined tolerance, there is a high probability that the two gases are the same.

SUMMARY OF THE INVENTION

In one aspect, generally, the invention features identifying an unknown gas by generating an infrared spectrum of the unknown gas using an infrared spectrophotometer that includes a circular variable interference filter, compressing the infrared spectrum of the unknown gas, and comparing the compressed infrared spectrum of the unknown gas to a library of compressed infrared spectra of reference compounds. In some embodiments, the spectrum of the unknown gas is normalized prior to compression to further ease comparison with the library of reference compounds.

Because the infrared spectrum of the unknown gas is generated using a circular variable interference filter, a relatively light weight instrument that can be operated on battery power and operates well even when faced with dirt, vibration, and other rigors of field operation, the invention is particularly useful when implemented as a portable system. Thus, the invention is of particular use to industrial hygienists and other safety personnel because it enables them to quickly identify gases and vapors in the field without incurring the expense and delays of transporting air samples to a laboratory for analysis. This, of course, reduces the risks of chemical exposure and allows immediate decisions to be made on remedial action. Moreover, use of the invention avoids the risk that reactive or absorption-prone samples will have decomposed or otherwise decayed in their sample containers before reaching the laboratory for analysis.

Though the circular variable interference filter is a relatively low resolution device, the invention allows a surprisingly reliable comparison of the spectrum of the unknown gas with a library of reference compound spectra obtained using higher resolution infrared spectrophotometers. This improves the accuracy of the comparison process because it ensures that the spectrum of the unknown gas is compared against highly accurate representations of the spectra of the reference compounds, even though the reference spectra were produced by a different technology.

The invention also features sampling the background air prior to sampling the unknown gas and modifying the infrared spectrum of the unknown gas to account for materials present in the background air. Thus, for example, if the identification of a gas is occurring in an area in which the background air has high levels of particular compounds—such as along a busy highway where auto exhaust fumes are at increased levels, use of the background air sample reduces any risk of misidentification that might result from the increased levels of those compounds.

In another aspect, the invention features identifying an unknown gas by generating an infrared spectrum of the unknown gas, compressing the infrared spectrum of the unknown gas, comparing the compressed infrared spectrum of the unknown gas to a library of compressed infrared spectra of reference compounds, and decompressing the compressed infrared spectra of reference compounds that most closely match the compressed infrared spectrum of the unknown gas, preferably the best three. The decompressed infrared spectra are then displayed with the infrared spectrum of the unknown gas for visual confirmation of the accuracy of the identification. The preferred compression ratio of 10:1 has been found to produce decompressed displayed spectra with a variance of only about 1% from the original.

In another aspect, the invention features identifying an unknown gas by producing a set of data corresponding to infrared characteristics of the unknown gas using an infrared spectrophotometer including a circular variable interference filter that includes a plurality of segments. Each of the segments transmits infrared energy across a frequency band from a starting frequency at a first end of the segment and to an ending frequency at a second end of the segment. An infrared spectrum of the unknown gas is then generated using the set of data and information designating the starting and ending frequencies of each of the segments of the variable interference filter. Finally, this infrared spectrum is compared to a set of infrared spectra in a library of reference compounds. Typically, the information designating the starting and ending frequencies of each of the segments is unique to a particular infrared spectrophotometer, i.e., the information varies from unit to unit.

DESCRIPTION OF THE PREFERRED EMBODIMENTS

Figure 1:
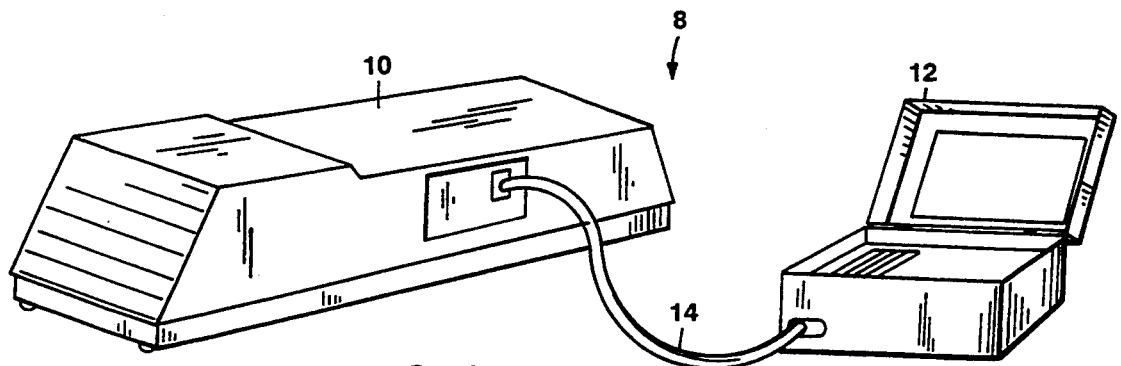
FIG. 1 shows a preferred embodiment of a portable unknown gas identification system according to the invention.

As shown in FIG. 1, a portable unknown gas identification system 8 includes a portable infrared spectrophotometer 10 such as the MIRAN 1B2 or 1BX produced by The Foxboro Company, of Foxboro, Massachusetts. Portable infrared spectrophotometer 10 is connected to a portable computer 12 via a serial cable 14. Portable computer 12 compares an infrared spectrum generated for an unknown gas by portable infrared spectrophotometer 10 to a stored library of spectra for approximately 400 reference compounds. In preferred embodiments, the spectra in this library are derived from infrared spectra obtained using high resolution spectrophotometers as well as from a variety of public domain sources. Based on comparison of the spectrum of the unknown gas with spectra in the library, portable computer 12 displays spectra for the unknown gas and for the three closest reference compounds. The displayed results allow a user to visually verify the accuracy of the closest matches.

Figure 2:
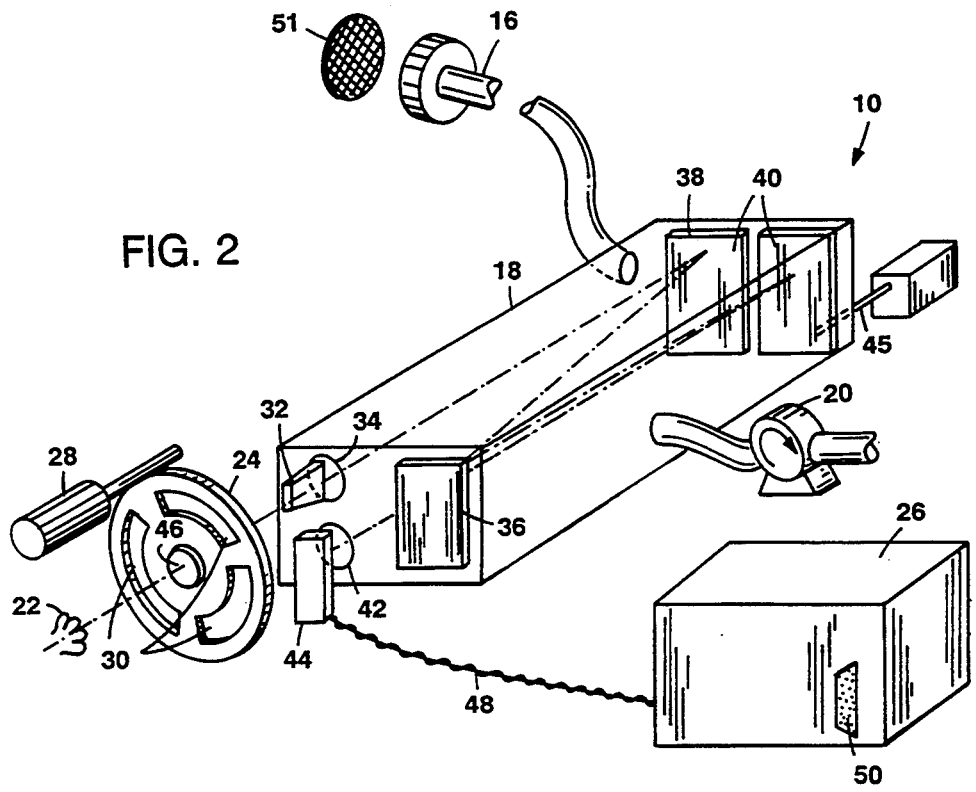
FIG. 2 is a cutaway perspective view of an infrared spectrophotometer used in the system of FIG. 1.

Referring also to FIG. 2, portable infrared spectrophotometer 10 includes a sample probe 16 through which gas samples are drawn into a gas cell 18 Via a suction line 20 connected to a source of suction (not shown). Broad-band infrared energy from a heated infrared source 22 is focussed on a circular variable interference filter ("CVF") 24. CVF 24 is slowly rotated under control of an electronics module 26, using a servo motor 28. As CVF 24 rotates, filter segments 30 are rotated between infrared source 22 and a light pipe 32.

Each filter segment 30 passes a continuous band of frequencies that varies from a starting frequency at one end of the filter segment 30 to an ending frequency at an opposite end of the filter segment 30. A particular location on a filter segment 30 transmits, for the most part, only a single frequency. Thus, as a filter segment 30 is rotated between infrared source 22 and light pipe 32, infrared energy in a series of single frequencies that vary from the starting frequency of the segment to the ending frequency of the segment is directed on light pipe 32.

Infrared energy passes through light pipe 32 and enters gas cell 18 via an entry window 34, and is reflected several times between reflective mirrors 36–40, before emerging via an exit window 42 and striking an infrared detector 44. A pushrod assembly 45 varies the angle of mirror 40, and thereby varies the pathlength of gas cell 18 and hence the sensitivity of the portable infrared spectrophotometer 10. (The sensitivity increases with increasing pathlength.) Though various pathlengths can be used, the embodiment described herein uses a pathlength of 6.75 meters.

Infrared detector 44 transmits a voltage signal to electronics module 26 via leads 48. This voltage signal corresponds to the level of infrared energy incident on infrared detector 44, and therefore corresponds to the absorption characteristics of the material in gas cell 18. Similarly, a servo potentiometer 46 transmits to electronics module 26 a voltage signal that corresponds to the angle of rotation of CVF 24 and can be used to determine the frequency of the infrared energy passing through gas cell 18 and incident on infrared detector 44. Electronics module 26 digitizes and stores corresponding values of the voltage signals as a set of approximately 750 data points (i.e., with each voltage signal from infrared detector 44, electronics module 26 stores the simultaneously occurring value of the voltage signal from servo potentiometer 46). Upon a request from portable computer 12, electronics module 26 transmits these data points to portable computer 12 over serial cable 14 via a serial port 50.

The attached microfiche appendix includes software for implementing the aspects of the invention performed by portable computer 12. The software is written in the widely available "C" programming language and is designed to require minimal memory so that portable computer 12 can be selected from a wide variety of computers such as DOS-based personal computers having 8088, 80286, 80386, 80486, or Pentium processors.

Portable computer 12 processes the data points from electronics module 26 and produces an infrared spectrum by converting the digitized voltages from servo potentiometer 46 to frequencies. Because the transmission characteristics of filter segments 30 vary from one CVF 24 to another, portable computer 12 uses conversion factors that identify characteristics of each filter segment 30 of a particular CVF 24. For example, for a CVF 24 having three filter segments 30, portable computer 12 is programmed with information about the range of voltage values from servo potentiometer 46 that correspond to each filter segment 30 of that CVF 24, and three sets of coefficients and conversion values. Thus, when the voltage value from servo potentiometer 46 is between voltage "A" and voltage "B", the voltage range for the first filter segment 30, portable computer 12 calculates the frequency by multiplying the voltage value by the coefficient for the first filter segment 30 and adding the constant for the first filter segment 30. Similarly, when the voltage is between voltages "C" and "D", the voltage range for the second filter segment 30, portable computer 12 calculates the frequency by multiplying the voltage value by the coefficient for the second filter segment 30 and adding the constant for the second filter segment 30. Finally, when the voltage is between voltages "E" and "F", the voltage range for the third filter segment 30, portable computer 12 calculates the frequency by multiplying the voltage value by the coefficient for the third filter segment 30 and adding the constant for the third filter segment 30.

Figure 3:
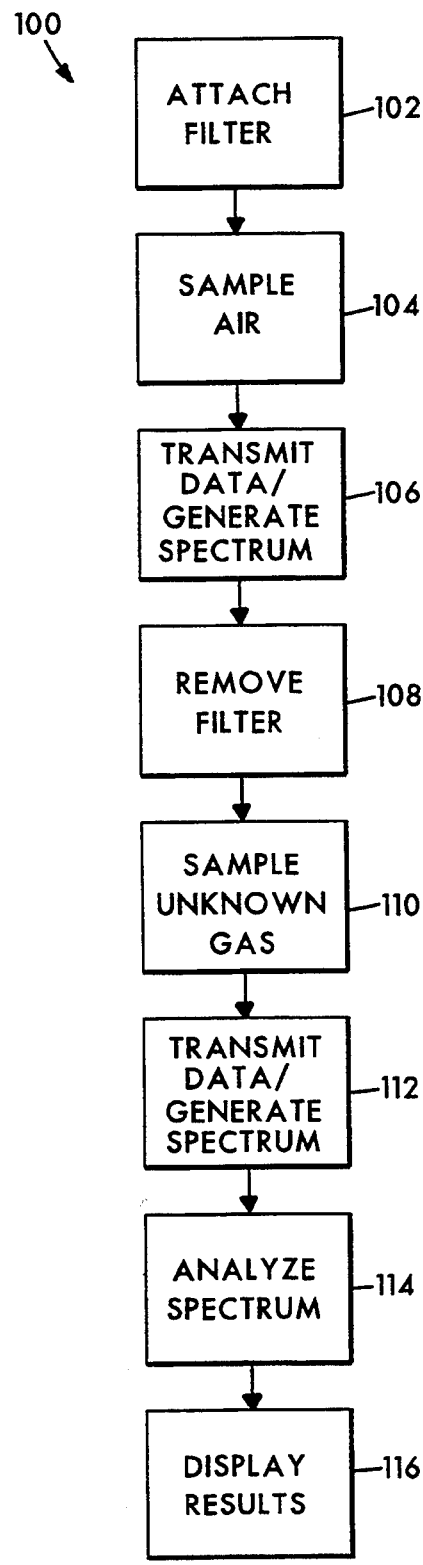
FIG. 3 is a block diagram of the procedure implemented by the system of FIG. 1.

System 8 identifies an unknown gas according to a procedure 100 shown in FIG. 3. First, an organic compound blocking filter such as a carbon filter 51 is attached to the end of sample probe 16 (step 102). Next, a sample of background air is drawn into portable infrared spectrophotometer 10 through sample probe 16 (step 104). (Carbon filter 51 ensures that organic compounds or other contaminants do not accompany the background air sample.) Portable infrared spectrophotometer 10 then generates data points from a full rotation of CVF 24 and transmits the data points to portable computer 12 which, using the procedure discussed above, then generates an infrared spectrum for the background air sample (step 106). Next, carbon filter 51 is removed (step 108) and a sample of an unknown gas is drawn into portable infrared spectrophotometer 10 through sample probe 16 (step 110). Thereafter, portable infrared spectrophotometer 10 generates and transmits data points from which portable computer 12 generates an infrared spectrum for the unknown gas (step 112). After generating the infrared spectrum for the unknown gas, portable computer 12 analyzes the infrared spectrum for the unknown gas in light of the infrared spectrum of the background air sample to determine the identity of the unknown gas (step 114). Finally, portable computer 12 displays the results of the analysis (step 116).

Figure 4:
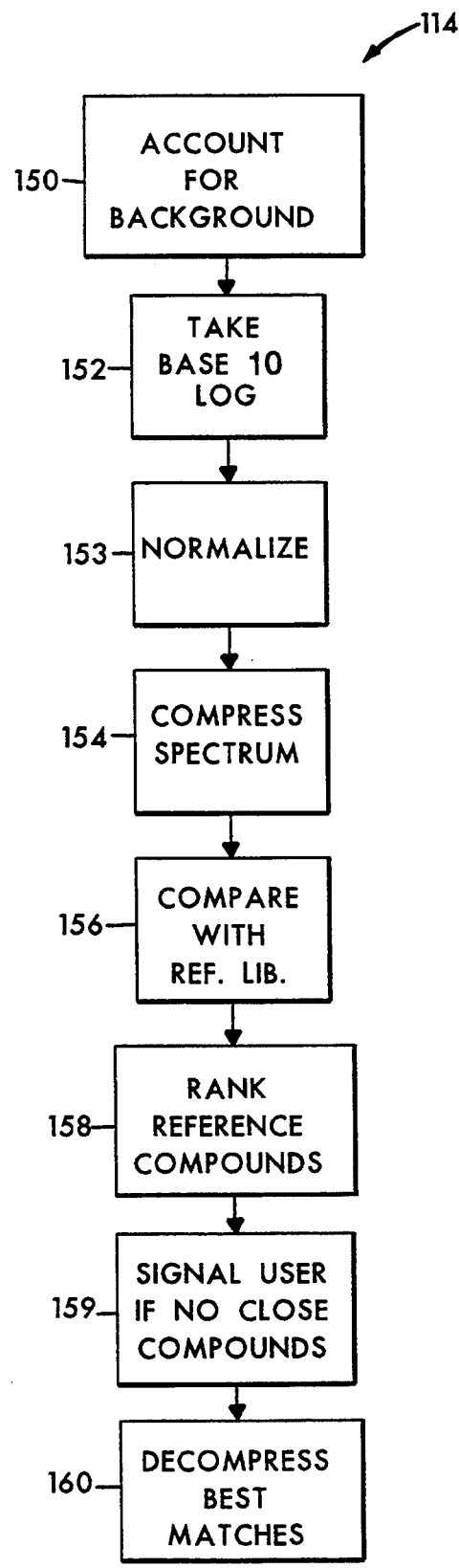
FIG. 4 is a block diagram of the procedure implemented by a computer of the system of FIG. 1 to analyze the infrared spectrum of an unknown gas.

FIG. 4 illustrates the procedure 114 used by portable computer 12 to identify the unknown gas. First, portable computer 12 divides each point of the infrared spectrum of the unknown gas by the value of the corresponding point of the infrared spectrum of the background air sample (step 150). This reduces any effect on identification of the unknown gas that would result from materials present in the background air that enters gas cell 18 with the unknown gas. Next, portable computer 12 calculates the base-10 logarithm of the resulting quotients (step 152). Portable computer 12 then divides each logarithm in the resulting set by the maximum logarithm in the set to produce a normalized infrared absorption spectrum for the unknown gas.

Because the spectra from the library of reference compounds have been compressed prior to insertion into the library, portable computer 12 compresses the infrared spectrum of the unknown gas (step 154). Spectral compression of the spectra of both the library and the unknown gas is achieved through a technique known as principal component analysis (alternatively known as eigenvector compression or Karhunen-Loeve transformation). Through principal component analysis, the spectra from the library of reference compounds are converted to a reduced size set of spectra (eigenvectors) that are combined to produce each of the original spectra according to a set of coefficients (factor scores) corresponding to each of the original spectra. Thus, the library of approximately 400 spectra, each having 750 data points, is compressed to 75 spectra (the eigenvectors) and approximately 400 sets of 75 coefficients (the factor scores). Moreover, 10:1 compression is achieved with minimal information loss—in this case, ninety nine percent of the information content of the original 400 or so spectra is maintained.

Spectral compression reduces the storage space required by the library of reference compounds by about an order of magnitude and, more importantly, substantially simplifies the process of comparing the spectrum of the unknown gas to those in the library (step 156). Rather than comparing a 750 data point spectrum to about 400 other 750 data point spectra, portable computer 12 only needs to compare the 75 factor scores corresponding to the spectra of the unknown gas to the 400 other sets of 75 factor scores. Thus, the number of comparisons is reduced by two orders of magnitude.

Portable computer 12 compares the spectra by determining the Euclidean distance between the compressed spectrum of the unknown gas and the compressed reference spectra. Portable computer 12 does so by calculating, for each compressed reference spectrum, the square root of the sum of the squares of the distances between each data point of the spectrum of the unknown gas and the corresponding data point in the compressed reference spectrum. Thereafter, portable computer 12 ranks the distances in descending order (step 158), with the reference compound having the smallest distance from the unknown gas being the most likely match. In the event that none of the reference compounds matches the unknown gas within a predefined tolerance, portable computer 12 warns the user of this situation before proceeding further (step 159). Finally, portable computer 12 decompresses the spectra of the unknown gas and the three closest matches (step 160) and displays these spectra for visual review (step 116 of FIG. 3).

Figure 5:
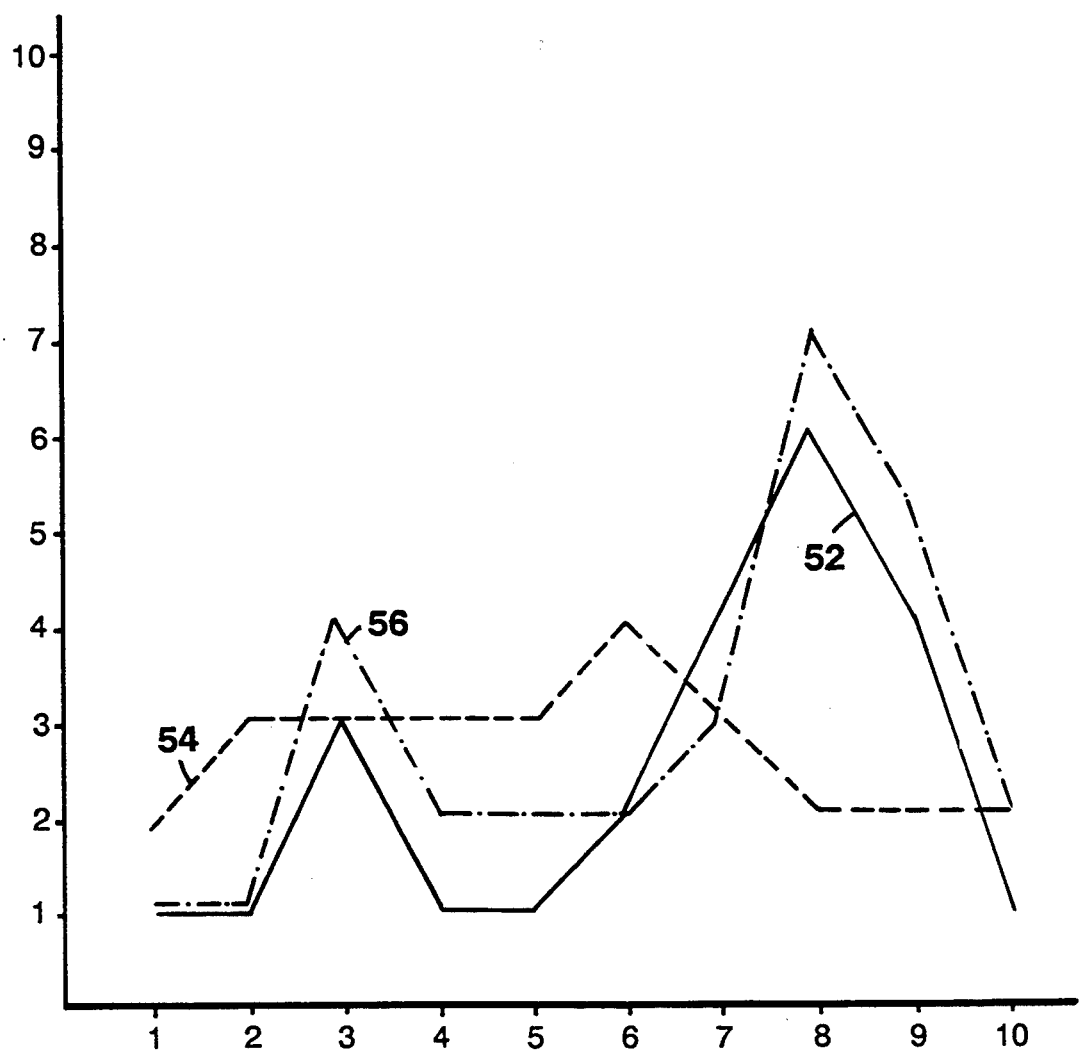
FIG. 5 is a graph showing representations of sample spectra for an unknown gas and two reference gases.

FIG. 5 illustrates the comparison procedure used by portable computer 12. For illustrative purposes, FIG. 5 shows comparison of the actual spectra. However, it should be understood that the same technique is used to compare the factor scores of the compressed spectra. The distance between the simplified spectrum for an unknown gas 52 and the simplified spectra for reference compounds 54, 56 are calculated as shown. For each data point, the differences between the spectra of the unknown gas and the reference compounds are determined (in actual embodiments, the differences between the factor scores are determined). These differences are then squared and summed to produce D54, which equals 39 and is the square of the distance between the unknown gas and reference gas 54, and D56, which equals 7 and is the square of the distance between the unknown gas and reference gas 56. In this case, as would be expected by a visual examination of the spectra, D54 is much larger than D56—indicating that reference gas 56 is a much closer match to the unknown gas than reference gas 54.

Figure 6:
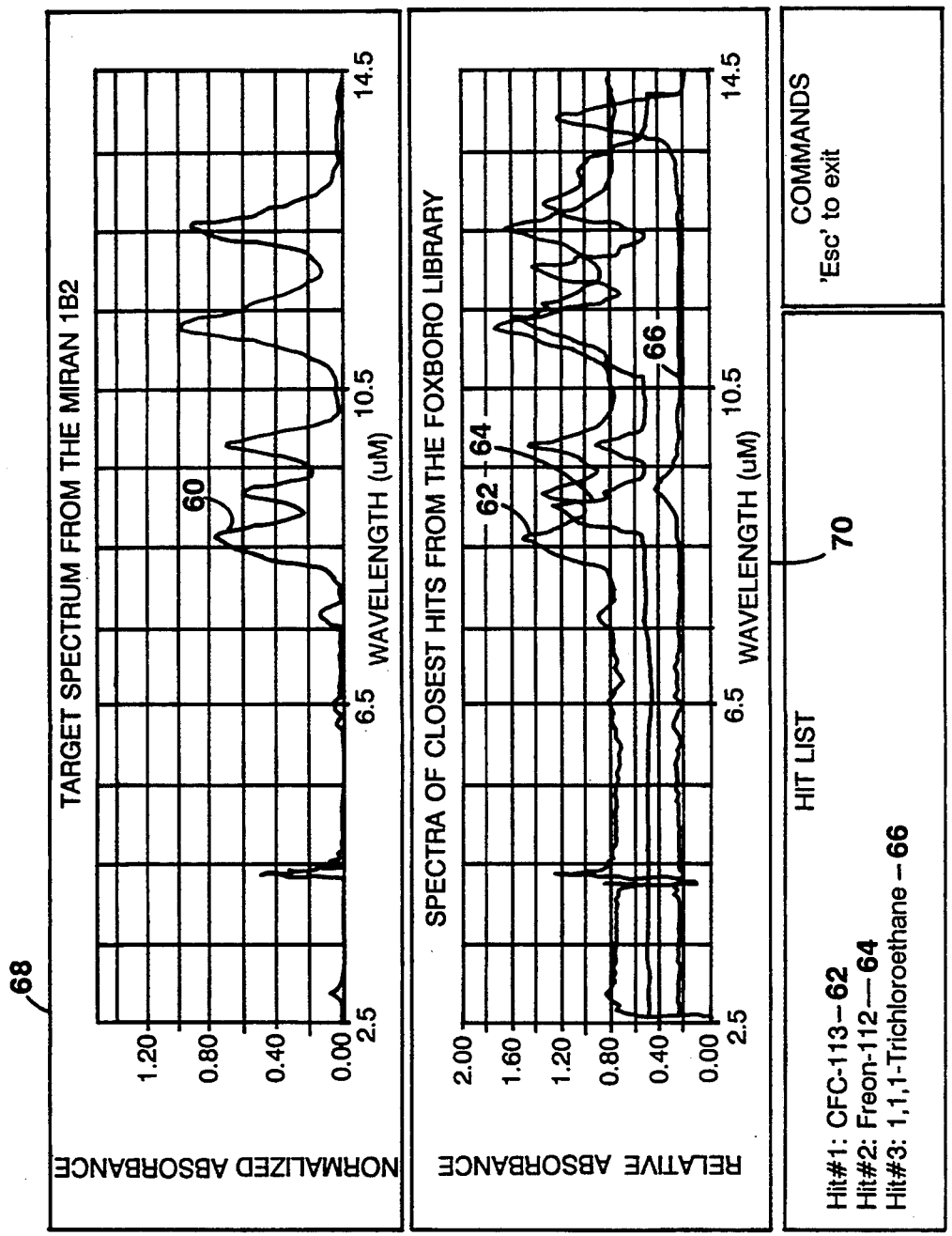
FIG. 6 is a representation of how infrared spectra are displayed to a user of the system of FIG. 1.

As shown in FIG. 6, the infrared spectrum 60 of Freon-113, the unknown gas in this example, is displayed in a first window 68 as a graph of normalized absorbance versus wavelength. Similarly, the infrared spectra of CFC-113 (62), Freon-112 (64), and 1,1,1-Trichloroethane (66), the three closest reference compounds, are displayed in a second window 70 as graphs of relative absorbance versus wavelength, with the graph of each spectra being offset to a different degree to ease distinction between the three compounds. Thus, the graph for CFC-113 (62) shows the normalized absorbance values for CFC-113 with an offset of 0.75 added to each the absorbance value at each frequency. The graphs for Freon-112 (64) and 1,1,1-Trichloroethane (66) are offset, respectively, by 0.5 and 0.25.

Other embodiments are within the following claims. For example, dedicated circuitry could be substituted for portable computer 12.

A portion of the disclosure of this patent document contains material which is subject to copyright protection. The copyright owner has no objection to the facsimile reproduction by anyone of the patent document or patent disclosure, as it appears in the Patent and Trademark Office file or records, but otherwise reserves all copyright rights whatsoever.

What is claimed is:

1. A method of identifying an unknown gas, comprising the steps of:

compressing infrared spectra from a set of infrared spectra of reference compounds to produce a library of compressed infrared spectra of reference compounds, generating an infrared spectrum of said unknown gas using an infrared spectrophotometer that includes a circular variable interference filter, compressing said infrared spectrum of said unknown gas, comparing said compressed infrared spectrum of said unknown gas to said compressed infrared spectra of reference compounds.

2. The method of claim 1, wherein said set of infrared spectra of reference compounds are compressed from infrared spectra obtained using an infrared spectrophotometer that does not include a circular variable interference filter and has higher resolution than said infrared spectrophotometer used in generating said infrared spectrum of said unknown gas.

3. The method of claim 1, wherein said generating step method further includes generating an infrared spectrum of a background air sample and modifying said infrared spectrum of said unknown gas based on said infrared spectrum of said background air sample.

4. The method of claim 1, wherein said generating step further includes normalizing said infrared spectrum of said unknown gas.

5. The method of claim 1, wherein said compressing steps use a compression ratio of about 10:1.

6. A method of identifying an unknown gas, comprising the steps of:

compressing infrared spectra from a set of infrared spectra of reference compounds to produce a library of compressed infrared spectra of reference compounds, generating an infrared spectrum of said unknown gas, compressing said infrared spectrum of said unknown gas, comparing said compressed infrared spectrum of said unknown gas to said compressed infrared spectra of reference compounds, decompressing a plurality of said compressed infrared spectra from said library, said plurality including the compressed infrared spectra that most closely match the compressed infrared spectrum of said unknown gas.

7. The method of claim 6, wherein said plurality of decompressed infrared spectra comprises the three most closely matching infrared spectra.

8. The method of claim 6, said method further including the step of displaying said plurality of decompressed infrared spectra.

9. The method of claim 8, said method further including the step of displaying said infrared spectrum of said unknown gas.

10. An apparatus for identifying an unknown gas, comprising:

an infrared spectrophotometer including a circular variable interference filter for producing an infrared spectrum of said unknown gas, circuitry for compressing said infrared spectrum of said unknown gas, a library of compressed infrared spectra of reference compounds compressed from infrared spectra obtained using an infrared spectrophotometer that does not include a circular variable interference filter and has higher resolution than said infrared spectrophotometer used in generating said infrared spectrum of said unknown gas, and circuitry for comparing said compressed infrared spectrum of said unknown gas to said compressed infrared spectra of reference compounds.

11. The apparatus of claim 10, wherein said apparatus is battery operated and portable.

12. An apparatus for identifying an unknown gas, comprising:

circuitry for compressing an infrared spectrum of said unknown gas, a library of compressed infrared spectra of reference compounds, circuitry for comparing said compressed infrared spectrum of said unknown gas to said compressed infrared spectra from said library, circuitry for decompressing a plurality of said compressed infrared spectra from said library, said plurality including the compressed infrared spectra that most closely match the compressed infrared spectrum of said unknown gas.

13. The apparatus of claim 12, said apparatus further including circuitry for displaying said plurality of decompressed infrared spectra.

14. The apparatus of claim 12, said apparatus further including circuitry for displaying said infrared spectrum of said unknown gas and said plurality of decompressed infrared spectra.

15. The apparatus of claim 12, wherein said apparatus is battery operated and portable.

* * * * *